United States Patent
Andersson et al.

(10) Patent No.: US 10,874,614 B1
(45) Date of Patent: *Dec. 29, 2020

(54) RAPIDLY DISINTEGRATING SOLID ORAL DOSAGE FORMS CONTAINING DASATINIB

(71) Applicant: XSPRAY PHARMA AB, Solna (SE)

(72) Inventors: Per Andersson, Uppsala (SE); Thomas Meijer, Segeltorp (SE); Victor Söderberg, Uppsala (SE)

(73) Assignee: XSPRAY PHARMA AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/004,107

(22) Filed: Aug. 27, 2020

Related U.S. Application Data

(63) Continuation of application No. 16/700,310, filed on Dec. 2, 2019, now Pat. No. 10,799,459.

(60) Provisional application No. 62/849,256, filed on May 17, 2019, provisional application No. 62/909,913, filed on Oct. 3, 2019.

(51) Int. Cl.
| | |
|---|---|
| *A61K 9/20* | (2006.01) |
| *A61K 9/00* | (2006.01) |
| *A61K 9/28* | (2006.01) |
| *A61K 31/506* | (2006.01) |

(52) U.S. Cl.
CPC .......... *A61K 9/2018* (2013.01); *A61K 9/0053* (2013.01); *A61K 9/28* (2013.01); *A61K 31/506* (2013.01)

(58) Field of Classification Search
CPC .. A61K 9/2018; A61K 9/0053; A61K 31/506; A61K 9/28
See application file for complete search history.

(56) References Cited

U.S. PATENT DOCUMENTS

| 7,125,875 B2 * | 10/2006 | Das ................ A61P 11/16 |
| | | 514/252.19 |
| 7,491,725 B2 | 2/2009 | Lajeunesse et al. |
| 7,973,045 B2 | 7/2011 | Teva |
| 8,884,013 B2 | 11/2014 | Yan et al. |
| 9,249,134 B2 | 2/2016 | Dwivedi et al. |
| 9,456,992 B2 | 10/2016 | Brisander et al. |
| 10,301,302 B2 | 5/2019 | Thirumalai |
| 10,464,933 B2 | 11/2019 | Thirunahari |
| 2008/0275009 A1 | 11/2008 | Chidambaram et al. |
| 2015/0057466 A1 | 2/2015 | Purohit et al. |

(Continued)

FOREIGN PATENT DOCUMENTS

| WO | 2010/062715 A2 | 6/2010 |
| WO | 2010/067374 A2 | 6/2010 |

(Continued)

OTHER PUBLICATIONS

Lowery et al., Assessment of tumor response to tyrosine kinase inhibitors, Front. Biosci. (2011) 16:1996-2007.

(Continued)

*Primary Examiner* — Trevor Love
(74) *Attorney, Agent, or Firm* — Merchant & Gould P.C.; Daniel R. Evans

(57) ABSTRACT

The instant application relates to the field of pharmaceutical compositions comprising dasatinb. Furthermore, the instant application relates to a method of treating proliferative disorders in a patient in need thereof, comprising administering a therapeutically effective amount of said compositions.

20 Claims, 2 Drawing Sheets

(56) References Cited

U.S. PATENT DOCUMENTS

| | | | |
|---|---|---|---|
| 2015/0133463 A1 | 5/2015 | Chiodo et al. |
| 2018/0186784 A1 | 7/2018 | Thirumalai |
| 2019/0040054 A1 | 2/2019 | Thirumalai |

FOREIGN PATENT DOCUMENTS

| | | | |
|---|---|---|---|
| WO | 2010/081443 A2 | 7/2010 |
| WO | 2010/139979 A2 | 9/2010 |
| WO | 2010/139980 A1 | 12/2010 |
| WO | 2010/139981 A2 | 12/2010 |
| WO | 2012/014149 A1 | 2/2012 |
| WO | 2013/065063 A1 | 5/2013 |
| WO | 2014/086326 A1 | 6/2014 |
| WO | 2017/002131 A1 | 1/2017 |
| WO | 2017/134615 A1 | 8/2017 |
| WO | 2017/134617 A1 | 8/2017 |
| WO | 2017/144109 A1 | 8/2017 |

OTHER PUBLICATIONS

Budha et al., Drug Absorption Interactions Between Oral Targeted Anticancer Agents and PPIs: Is pH-Dependent Solubility the Achilles Heel of Targeted Therapy?, Clin. Pharmacol. Ther. (2012) 92(2): 203-213.

Hervé J. Schwebel et al., The apparent solubilizing capacity of simulated intestinal fluids for poorly water-soluble drugs, Pharm. Dev. Technol. (2011) 16(3): 278-286.

Lassman et al., Phase 2 trial of dasatinib in target-selected patients with recurrent glioblastoma (RTOG 0627), Neuro-Oncology, (2015) 17(7): 992-998.

Public Assessment Report (Scientific Discussion) of Dasatinib film-coated tablets manufactured by Centrafarm B.V., published by College Ter Beoordeling van Geneesmiddelen on Dec. 6, 2018.

Vaidhyanathan et al., Bioequivalence Comparison of Pediatric Dasatinib Formulations and Elucidation of Absorption Mechanisms Through Integrated PBPK Modeling, J. Pharm. Sci. (2019) 108(1): 741-749.

Klingberg et al., Bioequivalence, Safety and Tolerability of Dasatinib Tablets 140 mg in Healthy Adult Volunteers under Fasting Conditions, J. Global Trends Pharm. Sci. (2016) 7(3): 3367-3373.

Chandani et al., Atypical pharmacokinetic profiles observed with dasatinib reference listed drug product in bioequivalence studies, AAPS Annual Meeting (2017) Poster M6107.

Fish et al., The Use of Experimental Design Principles in Dissolution Method Development: Development of a Discriminating Dissolution Method for Sprycel Film-Coated Tablets, J, Pharm. Innov. (2009) 4(4):165-173.

Dissolution Testing and Acceptance Criteria for Immediate-Release Solid Oral Dosage Form Drug Products Containing High Solubility Drug Substances; Guidance for Industry. U.S. Department of Health and Human Services Food and Drug Administration Center for Drug Evaluation and Research (CDER), Aug. 2018.

Referencing Approved Drug Products in ANDA Submissions FDA Guidance for Industry, Jan. 2017; 17 pgs.

FDA regulations, 21 CFR § 314.3, Apr. 2019; 7 pgs.

SPRYCEL® (dasatinib monohydrate) tablets prescribing information, Dec. 2018; 47 pgs.

Approved Drug Products with Therapeutic Equivalence Evaluations (in-part), 38th Edition, 2018; 9 pgs.

Pooja et al. DMF Filing in US, Europe and Canada, International Journal of Drug Regulatory Affairs (2015) 3(4): 9-17.

National Drug Code Directory 54893-0040-2, Dec. 2017; 5 pgs.

Federal Register, vol. 81, No. 169, Aug. 31, 2016, Requirements for Foreign and Domestic Establishment Registration and Listing for Human Drugs, Including Drugs That Are Regulated Under a Biologics License Application, and Animal Drugs; 55 pgs.

Bristol-Myers Squibb Co. v. Dr. Reddy's Labs. Ltd. et al., Civ. Act. No. 3:19-cv-18686, D.I. No. 1, filed Oct. 3, 2019 ("Bristol's Complaint").

Bristol-Myers Squibb Co. v. Dr. Reddy's Labs. Ltd. et al., Civ. Act. No. 3:19-cv-18686, D.I. No. 9, filed Nov. 1, 2019 ("DRL's Redacted Answer").

* cited by examiner

RAPIDLY DISINTEGRATING SOLID ORAL DOSAGE FORMS CONTAINING DASATINIB

RELATED APPLICATIONS

This application is continuation of U.S. patent application Ser. No. 16/700,310, filed Dec. 2, 2019, which claims priority to U.S. Provisional Application No. 62/849,256, filed on May 17, 2019 and U.S. Provisional Application No. 62/909,913, filed on Oct. 3, 2019.

FIELD

The instant application relates to the field of pharmaceutical compositions comprising dasatinb. Furthermore, the instant application relates to a method of treating proliferative disorders in a patient in need thereof, comprising administering a therapeutically effective amount of said compositions.

BACKGROUND

Many proliferative disorders, such as tumors and cancers, have been shown to involve overexpression or upregulation of protein kinase activity. Protein kinases are kinase enzymes that modify proteins by chemically adding phosphate groups (phosphorylation). Phosphorylation usually results in a functional change of the target protein by changing enzyme activity, cellular location, or association with other proteins. Protein kinases can be subdivided or characterised by the amino acids of the target protein whose phosphorylation they control: most kinases act on both serine and threonine, the tyrosine kinases act on tyrosine, and a number (dual-specificity kinases) act on all three. There are also protein kinases that phosphorylate other amino acids, including histidine kinases that phosphorylate histidine residues. The human genome contains about 500 protein kinase genes and up to 30% of all human proteins may be modified by protein kinases. Kinases are known to regulate the majority of cellular pathways, especially those involved in signal transduction. Dysregulation of protein kinases by mutation, gene rearrangement, gene amplification, and overexpression of both receptor and ligand has been implicated in the development and progression of human cancers. Protein kinase inhibiting compounds or protein kinase inhibitors (PKIs) are therefore useful for treating diseases caused by or exacerbated by overexpression or upregulation of protein kinases. For example, tyrosine kinase inhibitors have been shown be effective antitumor agents and anti-leukemic agents (Lowery A et. al., Front Biosci. 2011 Jun. 1; 17:1996-2007).

Drugs that are delivered orally via a tablet should ideally be readily soluble in water. Drugs that are poorly water-soluble tend to pass through the gastrointestinal tract before they can fully dissolve, and this typically leads to poor bioavailability of the drug. Unfortunately, many drugs currently on the market or in development are poorly water-soluble, and this presents a serious challenge to the pharmaceutical industry.

A major objective of formulation chemistry is to improve drug efficacy and safety, by e.g. improving bioavailability and stability as well as convenience to the patient. Bioavailability means the rate and extent to which an active substance or therapeutic is absorbed from a pharmaceutical form and becomes available at the site of action. The most common and preferred method of delivery due to convenience, ease of ingestion, and high patient compliance to treatment is the oral route of drug delivery. However, for certain drugs, drug absorption from the gastrointestinal tract is limited by poor aqueous solubility and/or poor membrane permeability of the drug molecules.

PKIs are generally weak bases that dissolve only at low pH (e.g. 100-1000 mg/L) and are practically insoluble at neutral pH (e.g. 0.1-10 mg/L). Typical PKIs exhibit non-polypeptide structure and have relatively low molecular weights, such as 10000 dalton or 5000 dalton.

pH-dependent solubility is a well-known issue for many oral formulations of poorly water-soluble substances, such as PKIs, since most of the absorption of the drug occurs in the small and large intestine, where pH is close to neutral. There is thus a continuing need to develop and improve the dissolution characteristics of oral solid dosage forms of PKI-based drugs. (Budha N R, Frymoyer A, Smelick G S, Jin J Y, Yago M R, Dresser M J, Holden S N, Benet L Z, Ware J A. Clin Pharmacol Ther. 2012 August; 92(2):203-13). Furthermore, it is important that the drug released from the solid phase does not precipitate in the gastrointestinal tract, or precipitates as little as possible, but remains soluble in the aqueous fluids of the gastrointestinal tract, since such precipitation results in low bioavailability (see e.g. Nerve J. et al. Pharm Dev Technol. 2011 June; 16(3):278-86).

Drug absorption from a solid dosage form after oral administration depends on i) the release of the drug substance from the drug product; ii) the dissolution or solubilization of the drug substance under physiological conditions; and iii) the permeation across the gastrointestinal membrane.

The Biopharmaceutics Classification System (BCS) is a system to differentiate drugs on the basis of their solubility and permeability.

BCS Class I consists of drugs with high permeability and high solubility. Class I compounds are well absorbed, and their absorption rate is usually higher than excretion.

BCS Class II consists of drugs with high permeability, but low solubility. The bioavailability of BCS class II drugs is limited by their solvation rate.

BCS Class III consists of drugs with low permeability, but high solubility. The absorption of BCS class III drugs is limited by the permeation rate but the drug is solvated very fast. If the formulation does not change the permeability or gastro-intestinal duration time, then class I criteria can be applied.

BCS Class IV consists of drugs low permeability and low solubility.

BCS class IV drugs have a poor bioavailability and are usually not well absorbed over the intestinal mucosa and a high variability is expected.

Dasatinib monohydrate, sold under the brand name Sprycel, is classified as a BCS II drug, i.e. having high permeability and low solubility. Dasatinib monohydrate is also considered to be a weakly basic drug that exhibits strong pH dependent solubility. Dasatinib monohydrate is currently presented in two drug product formulations, as an adult so-called immediate release tablet and a pediatric powder for oral suspension.

Solubility class boundaries are based on the highest dose strength of an immediate release product. A drug is considered highly soluble when the highest dose strength is soluble in 250 mL or less of aqueous media over the pH range of 1 to 6.8 at 37° C. (Dissolution Testing and Acceptance Criteria for Immediate-Release Solid Oral Dosage Form Drug Products Containing High Solubility Drug Substances; Guidance for Industry. U.S. Department of Health and Human Services Food and Drug Administration Center for Drug Evaluation and Research (CDER), August 2018). The volume estimate of 250 mL is derived from typical bioequivalence study protocols that prescribe administration of a drug product to fasting human volunteers with a glass of water.

Most conventional so-called immediate release oral drug products, such as tablets and capsules, are formulated to release the active drug immediately after oral administration. Immediate-release products generally result in relatively rapid drug absorption and onset of accompanying pharmacodynamic effects. Conventional immediate-release solid oral dosage form drug products containing high solubility drug substances are considered to be relatively low risk regarding the impact of dissolution on in vivo performance, provided the in vitro performance meets or exceeds the recommendations set by regulatory bodies, such as, for example, the U.S. Food and Drug Administration ("FDA") and the European Medicines Agency ("EMA").

For immediate release solid oral drug products containing a high solubility drug substance (as defined herein), the dissolution criterion is Q=80% in 30 minutes (Dissolution Testing and Acceptance Criteria for Immediate-Release Solid Oral Dosage Form Drug Products Containing High Solubility Drug Substances; Guidance for Industry. U.S. Department of Health and Human Services Food and Drug Administration Center for Drug Evaluation and Research (CDER), August 2018).

Drug product is a finished dosage form, e.g., tablet, capsule, or solution, that contains a drug substance, generally, but not necessarily, in association with one or more other ingredients (defined in Code of Federal Regulations Title 21, Sec 314.3(b)).

Background Regarding Dasatinib Monohydrate

Dasatinib monohydrate, sold under the brand name Sprycel, is a kinase inhibitor indicated for the treatment of:
  i) newly diagnosed adults with Philadelphia chromosome-positive (Ph+) chronic myeloid leukemia (CML) in chronic phase. The trial is ongoing and further data will be required to determine long-term outcome.
  ii) adults with chronic, accelerated, or myeloid or lymphoid blast phase Ph+CML with resistance or intolerance to prior therapy including imatinib; and
  iii) adults with Philadelphia chromosome-positive acute lymphoblastic leukemia (Ph+ALL) with resistance or intolerance to prior therapy.

Dasatinib monohydrate (Sprycel) was approved for medical use in the United States and in Europe in 2006.

SPRYCEL tablets are white to off-white, biconvex, film-coated tablets containing dasatinib monohydrate, with the following inactive ingredients:
  Lactose monohydrate
  Microcrystalline cellulose
  Croscarmellose sodium
  Hydroxypropyl cellulose, and
  Magnesium stearate.
The tablet coating consists of
  Hypromellose
  Titanium dioxide, and
  Polyethylene glycol.

Background Regarding Mechanism of Action

Dasatinib, at nanomolar concentrations, inhibits the following kinases: BCR-ABL, SRC family (SRC, LCK, YES, FYN), c-KIT, EPHA2, and PDGFRβ. Based on modeling studies, dasatinib is predicted to bind to multiple conformations of the ABL kinase.

In vitro, dasatinib was active in leukemic cell lines representing variants of imatinib mesylate sensitive and resistant disease. Dasatinib inhibited the growth of chronic myeloid leukemia (CML) and acute lymphoblastic leukemia (ALL) cell lines overexpressing BCR-ABL. Under the conditions of the assays, dasatinib was able to overcome imatinib resistance resulting from BCR-ABL kinase domain mutations, activation of alternate signaling pathways involving the SRC family kinases (LYN, HCK), and multi-drug resistance gene overexpression.

Background Regarding Dasatinib Forms

U.S. Pat. No. 7,491,725 (Bristol Myers Squibb) discloses a crystalline dasatinib monohydrate (H1-7), two crystalline anhydrate dasatinib (form N-6 and form T1H1-7), a crystalline n-butanolate (BU-2), a crystalline di-ethanolate (E2-1), and a crystalline hemi-ethanolate (T1E2-1).

U.S. Pat. No. 7,973,045 (Teva) discloses various solvates of dasatinib such as an n-propanol-dimethylsulfoxide ("DMSO") solvate of dasatinib, a DMSO solvate of dasatinib, a hemi tetrahydrofuran ("THF") solvate of dasatinib, a 2-methyl-tetrahydrofuran ("2-methyl THF") solvate of dasatinib, a hemi 1,4-dioxane solvate of dasatinib, a pyridine solvate of dasatinib, a toluene solvate of dasatinib, a methyl isobutyl ketone ("MIBK") solvate of dasatinib, a mono acetone solvate of dasatinib, an iso-propanol ("IPA")-DMSO solvate of dasatinib, a 2-butanol-DMSO solvate of dasatinib, an IPA-DMF solvate of dasatinib, an IPA solvate of dasatinib, an n-propanol-DMF solvate of dasatinib, an n-propanol solvate of dasatinib, a 2-butanol-DMF solvate of dasatinib, a 2-butanol solvate of dasatinib, an n-butanol-DMSO solvate of dasatinib, a DMF-water solvate of dasatinib, a DMF solvate of dasatinib, a methyl isopropyl ketone ("MIPK") solvate of dasatinib, a dimethoxyethane solvate of dasatinib, a cellosolve solvate of dasatinib, a methylacetate solvate of dasatinib, a methanol solvate of dasatinib, an ethylacetate solvate of dasatinib, a 2-pentanole solvate of dasatinib, a dimethyl carbonate solvate of dasatinib, an isopropylacetate solvate of dasatinib, a ethyleneglycol solvate of dasatinib, a dichloromethane solvate of dasatinib, a methylformate solvate of dasatinib, a tert-butanol solvate of dasatinib, a dimethoxyethane solvate of dasatinib, a methylethylketone ("MEK") solvate of dasatinib, a monochlorobenzene solvate of dasatinib, a propylene glycol monoethyl ether ("PGME") solvate of dasatinib, a glycerole solvate of dasatinib, a cyclopentyl methyl ether solvate of dasatinib, a methyl tert butyl ether ("MTBE") solvate of dasatinib, an amylalcohol solvate of dasatinib, and a glycerol formal solvate of dasatinib.

WO 2017/002131 (MSN) discloses a 1,2-propanediol solvate of dasatinib and WO 2017/134615 (Dr. Reddy) discloses a (R) and (S)-1,2-propanediol solvate of dasatinib.

WO 2017/144109 discloses an oral dosage form comprising dasatinib anhydrous N6 polymorph. It is further disclosed therein that when the disintegrant content is increased within a specific range, 0.3:1.0 to 0.5:1.0 based on the amount of dasatinib free base, then the dissolution of dasatinib N6 form from the dosage form decreases.

Dasatinib can thus be considered to a promiscuous compound with a high number of solvates. The monohydrate (H1-7), anhydrate (form N-6), anhydrate (form B, Teva) and 1,2-propanediol solvate (MSN) have all been tested in clinical trials on human beings.

Background Regarding Generic Drugs

A generic drug must contain the same active pharmaceutical ingredient as the original brand name product, but it may differ in characteristics such as manufacturing process, formulation, excipients, color, taste, and packaging.

Drug companies can submit an abbreviated new drug application (ANDA) for approval to market a generic drug that is the same as (or bioequivalent to) the brand-name product. FDA's Office of Generic Drugs reviews the application to make certain drug companies have demonstrated that the generic medicine can be substituted for the brand-name medicine.

An ANDA must show the generic medicine is equivalent to the brand in at least the following ways:
  i) The active ingredient is the same as that of the brand-name drug/innovator drug.
  ii) The generic medicine is the same strength.
  iii) The medicine is the same type of product (such as a tablet or an injectable).
  iv) The medicine has the same route of administration (such as oral or topical).
  v) It has the same use indications.
  vi) The inactive ingredients of the medicine are acceptable.

Some differences, which must be shown to have no effect on how the medicine functions, are allowed between the generic and the brand-name version.

The FDA defines bioequivalence as the absence of a significant difference in the rate and extent to which the active ingredient becomes available when administered at the same molar dose under similar conditions in an appropriately designed study.

In order to determine bioequivalence, a randomized, crossover trial is conducted with both the generic drug being assessed and the brand-name drug as the control. In these studies, a number of pharmacokinetic (PK) parameters are assessed, including maximum serum concentration of a drug (Cmax) and drug exposure over time (AUC).

These parameters help assess how the rate and extent of the availability of the generic drug compares to the control. As the FDA requires, there must be no significant difference in the rate and extent to be deemed bioequivalent.

According to current FDA and EMA guidance documents bioequivalence can be declared when the 90% confidence interval for the ratio of mean values for Cmax and AUC for generic drug vs. original drug falls within the interval 80-125%, as evaluated in a randomized, cross-over trial.

The confidence interval is dependent on both the point estimate for the ratio of mean values and on the variability between subjects in the PK parameter for each product. The larger the deviation in point estimate for the ratio from the value 1.0 and the larger the variability in the PK parameter between subjects for each product, the more unlikely it becomes that bioequivalence criteria will be met.

A ratio of mean values for Cmax and AUC for generic drug vs. original drug below 0.9 or above 1.1 will typically result in a 90% confidence interval outside 80-125% unless the variability in Cmax and AUC between subjects is very low. Therefore, the bioequivalence criteria are very strict and require that both the ratio of mean values is close to 1.0 and that the variability between subjects is limited.

According to an FDA study, the mean difference for AUC values between test and reference products was found to be 3.5% in the 2-year period following the Waxman-Hatch Act (Buehler G. History of bioequivalence for critical dose drugs. FDA).

In other words, it is a misconception that the FDA allows the strength of the tablet or a PK parameter, to vary from 80%-125%. The mean PK value of the generic drug must be quite close to that of the reference drug for the ratio of the PK values (AUC and Tmax) to be close to 1.00 which implies comparable bioavailability. If the ratio is not close to 1.00, then the 90% CI of ratio is unlikely to lie between 0.80 and 1.25.

Assessment of bioequivalence (BE) for highly variable drugs is challenging. Reference-scaled average bioequivalence (RSABE) is a statistical methodology that is increasingly used to demonstrate bioequivalence for highly variable drugs (HVDs). A drug product is called highly variable if the intra-subject (ie, within-subject) variability is greater than 30% C.V. (coefficient of variation) in the pharmacokinetic measures of AUC and/or Cmax. In other words, if you take the same drug in two different occasions at similar conditions (eg, same dosage, administration route, fasted, same time a day, etc.) you would expect the measured AUC and Cmax to be very similar regardless of the time of administration. However, if instead the rate and extend of absorption differ by more than 30% between the occasions then the drug is considered highly variable. In those cases, running ABE with the standard sample size will likely fail to show bioequivalence due to the intrinsic variability even if the products were comparable.

Indeed, some HVDs have failed to show bioequivalence to itself using standard ABE sample sizes. For HVDs, studies designed to show bioequivalence may need to enroll large numbers of subjects, even when the formulations themselves have no significant mean differences. This increases the expense of BE studies, places more subjects at risk, and ultimately, limits the availability of generics.

The RSABE method allows to scale the acceptance bioequivalence window based on the within subject variability of the reference drug. Thus, the limits of the conventional average bioequivalence (ABE) can be scaled to the reference variability (ie, the permitted window increases as the variability increases). RSABE methods can be applied to show bioequivalence if the within subject variability for the reference drug has been shown to have at least 30% CV.

Specifics of RSABE methodology vary between regulatory agencies. Simply stated, the RSABE may be employed if the reference product within-subject variability, $CV_{WR}$, is greater than 30%, which corresponds to a within-subject standard deviation $S_{WR} \geq 0.294$.

As related to AUC, if $S_{WR} \geq 0.294$, then RSABE may be permitted and acceptance criteria for 90% CI may be widened. The point estimate (or geometric mean ratio) must be within 80-125% regardless of the widened acceptance criteria.

As related to Cmax, if $S_{WR} \geq 0.294$, then RSABE may be permitted and acceptance criteria for 90% CI may be widened. The point estimate (or geometric mean ratio) must be within 80-125% regardless of the widened acceptance criteria.

In addition, most regulatory authorities would look at the intra-subject variability for the two products and ask questions if there was a marked difference between them. Products satisfying the bioequivalence requirements can reliably be assumed to produce similar clinical effects when used interchangeably in the same patient.

There is thus a high medical need and high commercial incentives for companies to develop a drug that is considered a generic drug according the relevant national regulatory standards. Such regulatory standards are high and difficult to meet since safety and efficacy is a major concern for all regulatory authorities. It is thus a major challenge to develop a drug that is considered fully bioequivalent and substitutable for the reference listed drug (RLD).

It is well established that Sprycel has a high PK variability. Lassman et al. (Phase 2 trial of dasatinib in target-selected patients with recurrent glioblastoma (RTOG 0627) in Neuro-Oncology, Volume 17, Issue 7, 1 Jul. 2015, Pages 992-998) discloses that dasatinib exposure is known to be quite variable within and between patients, with coefficients of variation of up to 100% for both AUC and Cmax.

There is notable interindividual heterogeneity in drug response, affecting both drug efficacy and toxicity, resulting in patient harm and the inefficient utilization of limited healthcare resources. It has been reported that the proportion of patients who respond beneficially to the first drug offered in the treatment of a wide range of diseases is typically just 50-75%. Drug absorption is an important component of drug response where interindividual variability leads to patient harm and the excessive and inefficient use of limited healthcare resources.

Background Regarding Dasatinib Bio-Equivalence Tests

The dasatinib monohydrate (H1-7) has been developed into Sprycel by BMS. All other dasatinib forms (anhydrate form N-6 [BMS], anhydrate form B, [Teva] and 1,2-propanediol solvate [MSN]) that have been tested in clinical studies for bio-equivalence vis-a-vis Sprycel have given a higher AUC compared to Sprycel. All forms have thus failed to meet the BE-standard of the entire 90% confidence interval (CI) of the observed PK value (AUC and Cmax) to fall between 80% and 125%. However, a generic version containing the anhydrate form N-6 was recently approved by EMA despite having an AUC with 90% confidence interval (CI) higher than 125% compared to Sprycel. Approval was only given after excluding some patients that showed an unexplained low exposure of dasatinib.

The Public Assessment Report on this medicinal product consisting of dasatinib film coated tablets from Centrafarm B.V. was published by College Ter Beoordeling van Geneesmiddelen on 6 Dec. 2018. The Public Assessment Report discloses the review performed on the quality, safety and efficacy data. The crystalline N-6 form of dasatinib was used as the active pharmaceutical ingredient (API) and the following additional excipients were used:

Tablet Core
  Cellulose, microcrystalline (E460)
  Lactose monohydrate
  Croscarmellose sodium
  Hydroxypropylcellulose (E463), and
  Magnesium stearate (E470b)
Film-Coating
  Poly(vinyl alcohol) (E1203)
  Titanium dioxide (E171)
  Talc (E553b)
  Glyceryl monostearate (E471), and
  Sodium laurylsulfate The first BE study was done with a 140 mg tablet and a simple cross-over study with 130 individuals. The test product gave too high AUC when all individuals were analyzed. The inter-individual was 48% for AUC and 62% for Cmax for the Sprycel tablet.

A four-way study in fasting was continued with each product given twice at a dose of 140 mg. This study also did not show formal bioequivalence. Numerical results are not shown in the Report.

In the analysis of data, it was found that the variability of AUC was greater for Sprycel than for the test product since Sprycel could provide very low exposures in some individuals. The new product was therefore approved by EMA despite deviation from formal BE because it gives a lower variability in AUC than Sprycel.

Vaidhyanathan et al. (Journal of Pharmaceutical Sciences 108 (2019) 741-749) discloses a bioequivalence comparison of a dasatinib suspension with commercial tablet (Sprycel) and elucidation of absorption mechanisms. A bioequivalence study comparing the formulations in adult healthy subjects found that overall exposure (AUC 0-24) from suspension treatments was ~9% to 13% lower, Cmax was similar, and median Tmax was ~30 min earlier vis-à-vis the tablet. To understand the mechanism contributing to this behavior a combination of biorelevant dissolution studies and physiologically based pharmacokinetic modeling was used and lead to the conclusion that that the mechanism that drives the reduced bioavailability of the suspension is inherent to the in vivo gastric behavior of the two different dosage forms. That is, the reduced bioavailability of the suspension was attributed to the shorter gastric residence time for suspensions relative to tablet and not related to the formulation composition or other drug product attributes.

Vaidhyanathan et al. uses a dissolution test where each formulation was introduced into 0.1 N HCl (stage 1) for 20 min followed by a switch to FaSSIFmedia (stage 2) to mimic the in vivo gastric to intestinal pH condition change in the fasted state. At stage 1, the test used 50 mL 0.1 N HCl (pH 1.2) for 20 min and at stage 2, added FaSSIF to reach 300 mL total final volume (1.2×FaSSIF preparation to accommodate dilution from the 0.1 N HCl). This 2-stage test with pH shift used a United States Pharmacopeia (USP) 2 apparatus at 75 RPM and 37° C. The volume of 50 mL in 0.1 N HCl followed by addition of 250 mL of 1.2×FaSSIF to reach a final volume of 300 mL was chosen to keep the volume low and approximate biorelevant conditions (representative of the dose volume and stomach).

Klingberg et al. (J Global Trends Pharm Sci, 2016; 7(3): 3367-3373) discloses a comparative BE study with Dasatinib tablets 140 mg originating from MSN Laboratories with reference formulation Sprycel® 140 mg film-coated tablet after single dose administration under fasting conditions in 24 healthy adult male and female volunteers. The two formulations were found to be non-bioequivalent since the 90% confidence interval for the (Test/Reference ratio) of $AUC_{0-t}$ and $C_{max}$ were 114.29%-224.24% and 108.85%-244.36% under fasting condition. The ratio of geometric least square means for the (Test/Reference ratio) of $AUC_{0-t}$ and $C_{max}$ were 160.08% and 163.08% under fasting condition.

Chandani et al. (Atypical pharmacokinetic profiles observed with dasatinib reference listed drug product in bioequivalence studies, poster M6107) discloses anomalous exposure profiles seen in small and inconsistent proportion of the panel within in-house dasatinib clinical. Overall the dasatinib product has consistently demonstrated erratic pharmacokinetic exposure profiles in 3.5%-7.5% in every in-house study, as well as very high Intra Subject Variability (ISCV) in AUC and Cmax. Chandani et al. concludes that for EU studies approximately 4.5% of subject data was excluded due to anomalous profile regulations. FDA outlier test carries a far more stringent criteria for PK data exclusion as compared to the EMA 5% rule; As a result, far fewer individual subject data sets would qualify for data exclusion based on the results of a studentized residuals outlier test.

There is thus an unmet need for a pharmaceutical composition that is bioequivalent to Sprycel (dasatinib monohydrate), but with fewer drawbacks like inter- or interindividual variation, food interaction, bioavailability dependent of gastric transit time and the like.

Fish et al., J Pharm Innov (2009) 4:165-173, discloses a dissolution method for Sprycel film-coated tablets. The method was developed to be a discriminatory method that not only could assess batch-to-batch variation but also be used to compare performance between dosage strengths that were not used in the clinic to clinical dosage strengths to support a biowaiver. The final validated method utilizes 1,000 mL of pH 4.0 acetate buffer with 1% Triton X-100 with a USP Apparatus II (paddle) rotating at 60 rpm and a HPLC sample analysis. The method was accepted by regulatory agencies globally for registrational testing of 20 and 50 mg tablets initially commercialized and has been successfully transferred to quality control laboratories in six countries around the world, according to the authors. The method has also been successfully applied to obtain biowaivers for 70 and 100 mg dosage strengths. It is thus reasonable to assume that this method would be used in producing a generic copy of Sprycel.

SUMMARY

One aspect is directed to a pharmaceutical composition for oral use comprising dasatinib, preferably dasatinib 1,2-propanediol solvate, dasatinib (R)-1,2-propanediol solvate, dasatinib (S)-1,2-propanediol solvate, or a combination thereof.

One embodiment of the present disclosure provides an oral pharmaceutical composition in the form of a tablet or a capsule.

One embodiment encompasses an oral pharmaceutical composition, wherein the pharmacokinetic profile of the dasatinib is less affected by the fed or fasted state of a subject ingesting the composition compared to Sprycel, in particular as defined by Cmax and AUC guidelines given by the FDA and EMA.

The amount of dasatinib can correspond to any of commercially available tablets sold under the trademark Sprycel, i.e. 20, 50, 70, 80, 100 or 140 mg. A conversion factor must be used to calculate the specific amount of for example dasatinib 1,2-propanediol solvate, or dasatinib 1,2-propanediol solvate (R) or (S) enantiomer that corresponds to 20, 50, 70, 80, 100 or 140 mg anhydrous dasatinib. 115.6 mg of dasatinib propylene glycol solvate is for example considered to be equivalent to 100 mg of anhydrous dasatinib, which corresponds to a conversion factor of about 1.156.

Bioequivalence of the oral compositions of the present disclosure may be established by a) 90% Confidence Interval for the ratio (generic drug vs reference listed drug) of mean AUC(0-t), which is between 80% and 125%; b) 90% Confidence Interval for the ratio (generic drug vs reference listed drug) of mean AUC(0-∞), which is between 80% and 125%; or c.) a 90% Confidence Interval for the ratio (generic drug vs reference listed drug) of mean Cmax, which is between 80% and 125%; or a combination of any features a-c above.

Alternatively, bioequivalence of the oral compositions of the present disclosure may be established by (a) a 90% Confidence Interval for the ratio (generic drug vs reference listed drug) of AUC(0-∞) is between 80% and 125%, and optionally without excluding any subjects with AUC(0-∞) <5% of the reference listed drug; (b) a 90% Confidence Interval the ratio (generic drug vs reference listed drug) of for Cmax, which is between 80% and 125%; and without excluding any subjects with AUC(0-t).; and (c) a 90% Confidence Interval the ratio (generic drug vs reference listed drug) of Cmax, which is between 80% and 125%; or a combination of any features a-c above.

Alternatively, bioequivalence of the oral compositions of the present disclosure may be established by reference-scaled average bioequivalence (RSABE) approach, whereby the BE acceptance limits are scaled to the variability of the reference product. For both the EMA and the FDA, RSABE can be employed if the reference product within-subject variability, $CV_{WR}$, is greater than 30%, which corresponds to a within-subject standard deviation $S_{WR} \geq 0.294$. Based on the intra-subject standard deviation of the reference formulation one can calculate the following scaled acceptance range limits:

| $CV_{WR}$ | $S_{WR}$ | FDA RSABE Limits |
|---|---|---|
| <30 | | ABE Methodology |
| 30 | 0.294 | 76.94-129.97 |
| 35 | 0.340 | 73.82-135.47 |
| 40 | 0.385 | 70.89-141.06 |
| 45 | 0.429 | 68.15-146.74 |
| 50 | 0.472 | 65.58-152.48 |
| 60 | 0.555 | 60.95-164.08 |

One embodiment of the present disclosure is the first dasatinib containing drug product that is independent of gastric transit time.

It is also the first dasatinib containing drug product that is AB rated therapeutic equivalent to Sprycel (dasatinib monohydrate), i.e. pharmaceutically equivalent since it contains the same active ingredient in the same dosage form, same strength or concentration and same route of administration, and also bioequivalent according to FDA standard.

Figure 1:
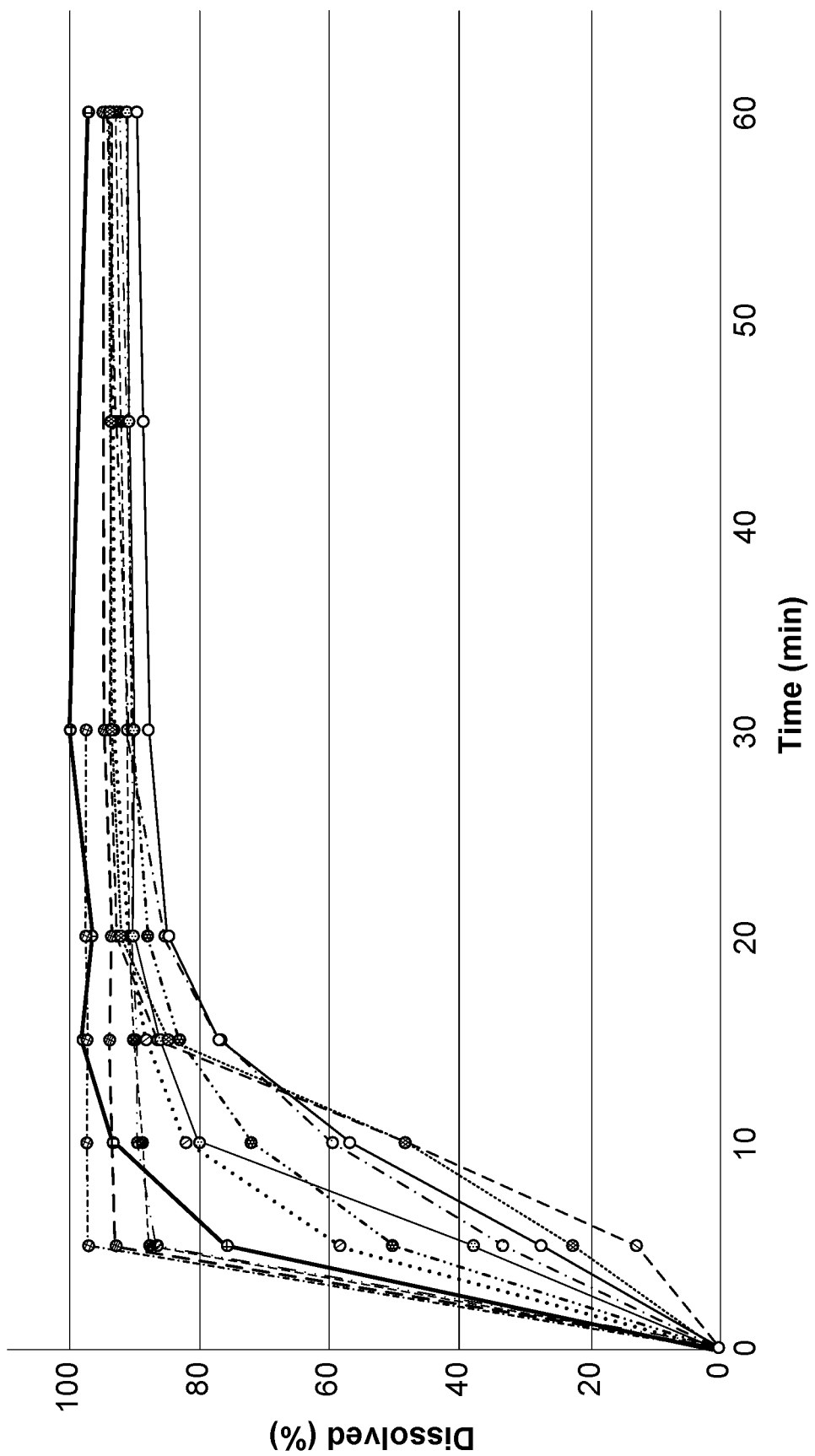
FIG. 1 provides results of a dissolution test, a USP Type 2 in 0.01 M hydrochloric acid at about 37° C. and about 75 RPM, of tablets prepared in Examples 1 to 13.

Both the foregoing general description and the following detailed description are exemplary and explanatory and are intended to provide further explanation of the disclosure as claimed. Other objects, advantages, and novel features will be readily apparent to those skilled in the art from the following detailed description.

DETAILED DESCRIPTION

In one aspect there is provided a tablet for oral administration, comprising dasatinib, such as dasatinib 1,2-propanediol solvate, dasatinib (R)-1,2-propanediol solvate, dasatinib (S)-1,2-propanediol solvate, or a combination thereof; and at least one pharmaceutically acceptable excipient;
wherein the tablet exhibits at least one of the following characteristics:
(a) a 90% Confidence Interval for the ratio of the mean AUC(0-∞) which is between 80% and 125%; and
(b) a 90% Confidence Interval for the ratio of the mean Cmax, which is between 80% and 125%;
(c) RSABE AUC criterion;
(d) RSABE Cmax criterion and;
(e) the tablet (coated or uncoated) releases at least 80% of the dasatinib within 20 minutes when the tablet is tested in a USP Type 2 in 0.1 M hydrochloric acid at about 37° C.;
wherein the ratio of the mean refers to an observable of the tablet for oral administration vs. the reference listed drug (SPRYCEL® 100 mg).

In one embodiment there is provided a tablet for oral administration, comprising dasatinib, such as dasatinib 1,2-propanediol solvate, dasatinib (R)-1,2-propanediol solvate, dasatinib (S)-1,2-propanediol solvate, or a combination thereof; and
at least one pharmaceutically acceptable excipient;

wherein the tablet (coated or uncoated) releases at least 80% of the dasatinib within 20 minutes when the tablet is tested in a USP Type 2 in 0.1 M hydrochloric acid at about 37° C.; and wherein the tablet exhibits at least one of the following characteristics:
(a) a 90% Confidence Interval for the ratio of the mean AUC(0-∞) which is between 80% and 125%; and
(b) a 90% Confidence Interval for the ratio of the mean Cmax, which is between 80% and 125%;
(c) RSABE AUC criterion;
(d) RSABE Cmax criterion and;
wherein the ratio of the mean refers to an observable of the tablet for oral administration vs. the reference listed drug (SPRYCEL® 100 mg).

In one embodiment the dasatinib is in the form of dasatinib 1,2-propanediol solvate.

In one embodiment the dasatinib is in the form of dasatinib 1,2-propanediol solvate (R) or (S) enantiomer, or a mixture thereof.

In one embodiment the dasatinib is in the form of dasatinib 1,2-propanediol solvate (S) enantiomer.

Dasatinib 1,2-propanediol solvate is also referred to as dasatinib propylene glycol solvate.

In one embodiment the dasatinib is administered to a human subject in a fasted state.

In one embodiment the dasatinib is administered to a human subject in a non-fasted state.

In one embodiment the bioequivalency is established by a 90% Confidence Interval for the ratio of the mean AUC (0-∞) which is between 80% and 125%.

In one embodiment the bioequivalency is established by a mean for AUC(0-∞) which is between 80% and 125%.

In one embodiment the bioequivalency is established by a 90% Confidence Interval for the ratio of the mean AUC (0-t) which is between 80% and 125%.

In one embodiment the bioequivalency is established by a mean for AUC(0-t) which is between 80% and 125%.

In one embodiment the bioequivalency is established by a 90% Confidence Interval for the ratio of the mean for Cmax, which is between 80% and 125%.

In one embodiment the bioequivalency is established by a mean for Cmax, which is between 80% and 125%.

In one embodiment the bioequivalency is established using the reference-scaled average bioeqvivalence (RSABE).

In one embodiment the bioequivalency is established without excluding any subjects.

In one embodiment the bioequivalency is established by excluding subjects with AUC (0-∞)<5% of the reference listed drug.

In one embodiment the bioequivalency is established by excluding subjects with AUC (0-t)<5% of the reference listed drug.

The dasatinib compositions of the present disclosure have unexpectedly dramatic dissolution profiles. Rapid dissolution of an administered active agent is preferable, as faster dissolution generally leads to faster onset of action and greater bioavailability. To improve the dissolution profile and bioavailability of dasatinib it would be useful to increase the drug's dissolution so that it could attain a level close to 100%.

The dasatinib compositions of the present disclosure preferably have a dissolution profile in which within about 5 minutes at least about 20% of the composition is dissolved. In other embodiments of the disclosure, at least about 30%, about 40%, about 50%, about 60%, about 70%, about 80%, about 90%, or about 100% of the dasatinib composition is dissolved within about 5 minutes. In other embodiments of the disclosure, preferably at least about 40%, about 50%, about 60%, about 70%, about 80%, about 90%, or about 100% of the dasatinib composition is dissolved within about 10 minutes. In another embodiment of the disclosure, preferably at least about 70%, about 80%, about 90%, or about 100% of the dasatinib composition is dissolved within about 15 minutes. In another embodiment of the disclosure, preferably at least about 70%, about 80%, about 90%, or about 100% of the dasatinib composition is dissolved within about 20 minutes.

Dissolution is preferably measured in a medium which is discriminating. Such a dissolution medium will produce two different dissolution curves for two products having different dissolution profiles in gastric juices; i.e., the dissolution medium is predictive of in vivo dissolution of a composition. An exemplary dissolution medium is an aqueous medium of 0.01 M hydrochloric acid at about 37° C., under so called USP Type 2 conditions i.e. a paddle speed of about 75 rpm in 500 mL. Determination of the amount dissolved can be carried out by any standard procedure recognized in the art.

Pharmaceutical Excipients

A pharmaceutical excipient is a substance formulated alongside the active ingredient of a medication, included for example for the purpose of long-term stabilization, bulking up solid formulations that contain potent active ingredients in small amounts (thus often referred to as "bulking agents", "fillers", or "diluents"), or to confer a therapeutic enhancement on the active ingredient in the final dosage form, such as facilitating drug absorption, reducing viscosity, or enhancing solubility. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life.

Fillers/Binders

Fillers add bulk to tablets making small amounts active components easier to handle during the manufacturing process. Binders hold the ingredients in a tablet together. Binders ensure that tablets and granules can be formed with required mechanical strength and give volume to low active dose tablets. Many pharmaceutical excipients have dual functionality and fillers and binders are thus often often treated as one group of pharmaceutical excipients, i.e. fillers/binders. Suitable fillers/binders are different grades of mannitol, microcrystalline cellulose, lactose, isomalt or mixtures thereof. Suitable amounts of fillers/binders are about 20-90% by weight, about 30-80% by weight, about 40-70% by weight, and about 50-60% by weight.

Disintegrants

Disintegrants swell, expand and/or dissolve when wet causing the tablet to break apart in the digestive tract, or in specific segments of the digestion process, releasing the active ingredients for absorption. Suitable disintegrants, such as croscarcellose sodium, crospovidone, and sodium starch glycolate, or mixtures thereof may be used. Suitable amounts of disintegrants are about 0.5-10% by weight, about 1-9% by weight, about 2-8% by weight, about 3-7% by weight, about 4-6% by weight, and about 5% by weight.

Glidants

Glidants are used to promote powder flow by reducing interparticle friction and cohesion. Glidants are often used in combination with lubricants as they have small ability to reduce die wall friction. Any conventional glidant, such as anhydrous colloidal silica may be used. Suitable amounts of glidants are about 0-5% by weight, about 1-4% by weight and about 2-3% by weight.

Lubricants

Lubricants prevent the clumping of active ingredients and prevent the sticking of materials to machines in the manufacturing process. Any conventional lubricant, such as sodium stearyl fumerate or magnesium stearate may be used. Suitable amounts of lubricants are about 0-5% by weight, about 1-4% by weight and about 2-3% by weight.

Coatings

Coatings protect tablet ingredients from deterioration by moisture in the air and make large or unpleasant-tasting tablets easier to swallow. Any conventional coating material, such as different grades of Opadry may be used. Opadry is a mixture consisting of mainly hypromellose, macrogol 400 and Polysorbate 80. Any conventional coating method, like spraying may be used. Colors are sometimes added to improve the appearance of a tablet. Color consistency is important as it allows easy identification of a medication. Some coatings are therefore colored using Opadry Blue or Opadry White, wherein titanium dioxide is the white color agent.

In another embodiment, there is provided a composition, for use in therapy.

In another embodiment, there is provided a composition, for use in the treatment of proliferative disorders. Typically, said proliferative disorder is selected from tumors and cancers, including, but not limited to, neurofibromatosis, tuberous sclerosis, hemangiomas and lymphangiogenesis, cervical, anal and oral cancers, eye or ocular cancer, stomach cancer, colon cancer, bladder cancer, rectal cancer, liver cancer, pancreas cancer, lung cancer, breast cancer, cervix uteri cancer, corpus uteri cancer, ovary cancer, prostate cancer, testis cancer, renal cancer, brain cancer, cancer of the central nervous system, head and neck cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, multiple myeloma; cardiac hypertrophy, age-related macular degeneration and diabetic retinopathy.

More typically said proliferative disorder is selected from newly diagnosed adults with Philadelphia chromosome-positive (Ph+) chronic myeloid leukemia (CML) in chronic phase; adults with chronic, accelerated, or myeloid or lymphoid blast phase Ph+CML with resistance or intolerance to prior therapy including imatinib; adults with Philadelphia chromosome-positive acute lymphoblastic leukemia (Ph+ALL) with resistance or intolerance to prior therapy.

In another embodiment of this aspect, there is provided a composition of, said composition is provided during food intake.

In another aspect, there is provided a method of treating proliferative disorder in a patient in need thereof, comprising administering a therapeutically effective amount of a composition according to the present disclosure. Said proliferative disorder is typically selected from tumors and cancers including, but not limited to, neurofibromatosis, tuberous sclerosis, hemangiomas and lymphangiogenesis, cervical, anal and oral cancers, eye or ocular cancer, stomach cancer, colon cancer, bladder cancer, rectal cancer, liver cancer, pancreas cancer, lung cancer, breast cancer, cervix uteri cancer, corpus uteri cancer, ovary cancer, prostate cancer, testis cancer, renal cancer, brain cancer, cancer of the central nervous system, head and neck cancer, throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, multiple myeloma; cardiac hypertrophy, age-related macular degeneration and diabetic retinopathy.

Said proliferative disorder is more typically selected from newly diagnosed adults with Philadelphia chromosome-positive (Ph+) chronic myeloid leukemia (CML) in chronic phase; adults with chronic, accelerated, or myeloid or lymphoid blast phase Ph+CML with resistance or intolerance to prior therapy including imatinib; adults with Philadelphia chromosome-positive acute lymphoblastic leukemia (Ph+ALL) with resistance or intolerance to prior therapy.

The desired dose is conveniently presented in a single dose or as a divided dose administered at appropriate intervals, for example as two, three, four or more doses per day. Dependent on the need of the treatment and/or prevention, the desired dose may also be, for example, once every two days, once every three days, or even once a week.

The composition is conveniently administered in unit dosage form; for example containing 20 to 140 mg, conveniently as 20, 50, 70, 80, 100, or 140 mg of active ingredient per unit dosage form.

Pharmaceutical compositions include but are not limited to those suitable for oral, rectal, nasal, topical (including buccal and sub-lingual), transdermal, vaginal or parenteral (including intramuscular, subcutaneous and intravenous) administration or in a form suitable for administration by inhalation or insufflation. The compositions may, where appropriate, be conveniently presented in discrete dosage units and may be prepared by any of the methods well known in the art of pharmacy. Pharmaceutical compositions suitable for oral administration are conveniently presented as discrete units such as capsules, cachets or tablets, each containing a predetermined amount of the active substance.

Tablets for oral administration may contain conventional excipients such as binding agents, fillers, lubricants, disintegrants, or wetting agents. The tablets may be coated according to methods well known in the art.

The following examples are provided to illustrate various embodiments of the disclosure and shall not be considered as limiting in scope.

By the phrase "reference listed drug" is meant the approved drug product Sprycel 100 mg to which new generic versions are compared to show that they are bioequivalent. By designating a single reference listed drug as the standard to which all generic versions must be shown to be bioequivalent, FDA hopes to avoid possible significant variations among generic drugs and their brand name counterpart.

EXAMPLES

Example 1

A tablet was prepared based on the following recipe and direct compression:

| Component | Function | mg/tablet |
|---|---|---|
| Dasatinib 1,2-propanediol solvate | Drug substance | 115.00 |
| Mannitol (Roquette 200 SD) | Filler/Binder | 255.00 |
| Microcrystalline cellulose | Filler/Binder | 50.00 |
| Croscarmellose sodium | Disintegrant | 50.00 |
| Silica colloidal anhydrous | Glidant | 10.00 |
| Sodium Stearyl fumerate | Lubricant | 20.00 |
| Core tablet weight | | 500 |
| Opadry white | Cosmetic coat | 10.00 |
| Film coated tablet weight | | 510 |

Example 2

A tablet was prepared based on the following recipe and direct compression:

| Component | Function | mg/tablet |
|---|---|---|
| Dasatinib 1,2-propanediol solvate | Drug substance | 113.00 |
| Mannitol (Roquette 200 SD) | Filler/Binder | 280.60 |
| Microcrystalline cellulose | Filler/Binder | 48.00 |
| Croscarmellose sodium | Disintegrant | 9.60 |
| Silica colloidal anhydrous | Glidant | 9.60 |
| Sodium Stearyl fumerate | Lubricant | 19.20 |
| Core tablet weight | | 480 |
| Opadry white | Cosmetic coat | 10.00 |
| Film coated tablet weight | | 490 |

Example 3

A tablet was prepared based on the following recipe and direct compression:

| Component | Function | mg/tablet |
|---|---|---|
| Dasatinib 1,2-propanediol solvate | Drug substance | 113.00 |
| Mannitol (Roquette 500 DC) | Filler/Binder | 280.60 |
| Microcrystalline cellulose | Filler/Binder | 48.00 |
| Croscarmellose sodium | Disintegrant | 9.60 |
| Silica colloidal anhydrous | Glidant | 9.60 |
| Sodium Stearyl fumerate | Lubricant | 19.20 |
| Core tablet weight | | 480 |
| Opadry white | Cosmetic coat | 10.00 |
| Film coated tablet weight | | 490 |

Example 4

A tablet was prepared based on the following recipe and direct compression:

| Component | Function | mg/tablet |
|---|---|---|
| Dasatinib 1,2-propanediol solvate | Drug substance | 113.00 |
| Mannitol (Roquette 200 SD) | Filler/Binder | 164.30 |
| Microcrystalline cellulose | Filler/Binder | 164.30 |
| Croscarmellose sodium | Disintegrant | 9.60 |
| Silica colloidal anhydrous | Glidant | 9.60 |
| Sodium Stearyl fumerate | Lubricant | 19.20 |
| Core tablet weight | | 480 |
| Opadry white | Cosmetic coat | 10.0 |
| Film coated tablet weight | | 490 |

Example 5

A tablet was prepared based on the following recipe and direct compression:

| Component | Function | mg/tablet |
|---|---|---|
| Dasatinib 1,2-propanediol solvate | Drug substance | 115.60 |
| Mannitol (Roquette Pearlitol 200 SD) | Filler/Binder | 254.00 |
| Microcrystalline cellulose | Filler/Binder | 44.00 |
| Silica colloidal anhydrous | Glidant | 8.80 |
| Sodium Stearyl fumerate | Lubricant | 17.60 |
| Core tablet weight | | 440 |
| Opadry white | Cosmetic coat | 10.00 |
| Film coated tablet weight | | 450 |

Example 6

A tablet was prepared based on the following recipe and direct compression:

| Component | Function | mg/tablet |
|---|---|---|
| Dasatinib 1,2-propanediol solvate | Drug substance | 115.60 |
| Calcium Phosphate dibasic anhydrous | Filler/Binder | 44.00 |
| Microcrystalline cellulose | Filler/Binder | 254.00 |
| Silica colloidal anhydrous | Glidant | 8.80 |
| Sodium Stearyl fumerate | Lubricant | 17.60 |
| Core tablet weight | | 440 |
| Opadry white | Cosmetic coat | 10.00 |
| Film coated tablet weight | | 450 |

Example 7

A tablet was prepared based on the following recipe and direct compression:

| Component | Function | mg/tablet |
| --- | --- | --- |
| Dasatinib 1,2-propanediol solvate | Drug substance | 115.60 |
| Isomalt | Filler/Binder | 44.00 |
| Microcrystalline cellulose | Filler/Binder | 254.00 |
| Silica colloidal anhydrous | Glidant | 8.80 |
| Sodium Stearyl fumerate | Lubricant | 17.60 |
| Core tablet weight | | 440 |
| Opadry white | Cosmetic coat | 10.00 |
| Film coated tablet weight | | 450 |

Example 8

A tablet was prepared based on the following recipe and direct compression:

| Component | Function | mg/tablet |
| --- | --- | --- |
| Dasatinib 1,2-propanediol solvate | Drug substance | 115.60 |
| Isomalt | Filler/Binder | 254.00 |
| Microcrystalline cellulose | Filler/Binder | 44.00 |
| Silica colloidal anhydrous | Glidant | 8.80 |
| Sodium Stearyl fumerate | Lubricant | 17.60 |
| Core tablet weight | | 440 |
| Opadry white | Cosmetic coat | 10.00 |
| Film coated tablet weight | | 450 |

Example 9

A tablet was prepared based on the following recipe and direct compression:

| Component | Function | mg/tablet |
| --- | --- | --- |
| Dasatinib 1,2-propanediol solvate | Drug substance | 115.60 |
| Isomalt | Filler/Binder | 245.20 |
| Microcrystalline cellulose | Filler/Binder | 44.00 |
| Croscarmellose | Disintegrant | 8.80 |
| Silica colloidal anhydrous | Glidant | 8.80 |
| Sodium Stearyl fumerate | Lubricant | 17.60 |
| Core tablet weight | | 440 |
| Opadry white | Cosmetic coat | 10.00 |
| Film coated tablet weight | | 450 |

Example 10

A tablet was prepared based on the following recipe and direct compression:

| Component | Function | mg/tablet |
| --- | --- | --- |
| Dasatinib 1,2-propanediol solvate | Drug substance | 115.60 |
| Isomalt | Filler/Binder | 125.90 |
| Mannitol (Pearlitol 200 SD) | Filler/Binder | 125.90 |
| Microcrystalline cellulose | Filler/Binder | 44.00 |
| Croscarmellose | Disintegrant | 2.20 |
| Silica colloidal anhydrous | Glidant | 8.80 |
| Sodium Stearyl fumerate | Lubricant | 17.60 |
| Core tablet weight | | 440 |
| Opadry white | Cosmetic coat | 10.00 |
| Film coated tablet weight | | 450 |

Example 11

A tablet was prepared based on the following recipe and direct compression:

| Component | Function | mg/tablet |
| --- | --- | --- |
| Dasatinib 1,2-propanediol solvate | Drug substance | 115.60 |
| Isomalt | Filler/Binder | 125.90 |
| Mannitol (Pearlitol 200 SD) | Filler/Binder | 125.90 |
| Microcrystalline cellulose | Filler/Binder | 44.00 |
| Croscarmellose | Disintegrant | 2.20 |
| Silica colloidal anhydrous | Glidant | 8.80 |
| Sodium Stearyl fumerate | Lubricant | 17.60 |
| Core tablet weight | | 440 |
| Opadry white | Cosmetic coat | 10.00 |
| Film coated tablet weight | | 450 |

Example 12

A tablet was prepared based on the following recipe and direct compression:

| Component | Function | mg/tablet |
| --- | --- | --- |
| Dasatinib 1,2-propanediol solvate | Drug substance | 115.6 |
| Mannitol (Pearlitol 200 SD) | Filler/Binder | 72.0 |
| Mannitol (Pearlitol 300 DC) | Filler/Binder | 72.0 |
| Isomalt | Filler/Binder | 96.8 |
| Microcrystalline cellulose | Filler/Binder | 44.0 |
| Croscarmellose sodium | Disintegrant | 13.2 |
| Silica colloidal anhydrous | Glidant | 8.8 |
| Sodium Stearyl fumerate | Lubricant | 17.6 |
| Core tablet weight | | 440 |
| Opadry white | Cosmetic coat | 10.0 |
| Film coated tablet weight | | 450 |

Example 13

A tablet was prepared based on the following recipe and direct compression:

| Component | Function | mg/tablet |
|---|---|---|
| Dasatinib 1,2-propanediol solvate | Drug substance | 115.6 |
| Mannitol (Pearlitol 200 SD) | Filler/Binder | 77.0 |
| Mannitol (Pearlitol 300 DC) | Filler/Binder | 77.0 |
| Isomalt | Filler/Binder | 100.0 |
| Microcrystalline cellulose | Filler/Binder | 44.0 |
| Silica colloidal anhydrous | Glidant | 8.8 |
| Sodium Stearyl fumerate | Lubricant | 17.6 |
| Core tablet weight | | 440 |
| Opadry white | Cosmetic coat | 10.0 |
| Film coated tablet weight | | 450 |

The tablets prepared above (non-coated) were subjected to a dissolution test, a USP Type 2 in 0.01 M hydrochloric acid at about 37° C. and about 75 RPM, or as per Ph. Eur. 2.9.3. apparatus II (paddles), and the results are shown in FIG. 1. The results are representative for the present disclosure.

Example 14

Tablets of Example 12 and 13 were manufactured using the following process

The mannitol (Pearlitol 200 SD), mannitol (Pearlitol 300 DC), isomalt, microcrystalline cellulose, croscarmellose sodium and aerosil 200 were transferred to a suitably sized mixing vessel and blended. The resulting excipient blend mixture was then screened. The active component, dasatinib 1,2-propanediol solvate, was screened and added to the blend mixture in a suitably sized mixing vessel and blended. Sodium stearyl fumarate was screened and added to the blend mixture. This was then blended. The Dasatinib 1,2-propanediol solvate tablet blend was compressed into tablets. The resultant tablets were then coated with an aqueous film coating (Opadry®White 03628796 and sterile water for irrigation mixture).

Example 15

Tablets prepared according to Example 12 using the process of Example 14 were used in a single centre, open-label, randomised, single dose, 3-way crossover comparative PK study in healthy male subjects.

Each subject received the following regimens:

| Period | Regimen | Product | Dose | Route of Administration |
|---|---|---|---|---|
| | A | Tablet A | 100 mg | Oral, Fasted |
| | A | Tablet A | 100 mg | Oral, Fed |

Plasma concentration data was tabulated and plotted for each subject for whom concentrations are quantifiable. PK analysis of the concentration time data obtained was performed using appropriate non-compartmental techniques to obtain estimates of the following PK parameters, where possible:

Tlag: Time prior to the first measurable (non-zero) concentration
Tmax: Time of maximum observed concentration
Cmax: Maximum observed concentration
C24: Plasma concentration at 24 h
AUC(0-last): Area under the curve from 0 time to the last measurable concentration
AUC(0-24): Area under the curve from 0 time to 24 h post-dose
AUC(0-inf): Area under the curve from 0 time extrapolated to infinity
Frel: Relative bioavailability
λz: Slope of the apparent elimination phase
T1/2: Apparent elimination half-life
MRT: mean residence time Results

| Variable | Product | Mean | Median | Min | Max | CV % |
|---|---|---|---|---|---|---|
| Cmax | A fasted | 89 | 80 | 28 | 169 | 47 |
| | A fed | 100 | 85 | 36 | 214 | 49 |
| AUCinf | A fasted | 342 | 331 | 146 | 588 | 33 |
| | A fed | 413 | 390 | 301 | 732 | 29 |

Figure 2:
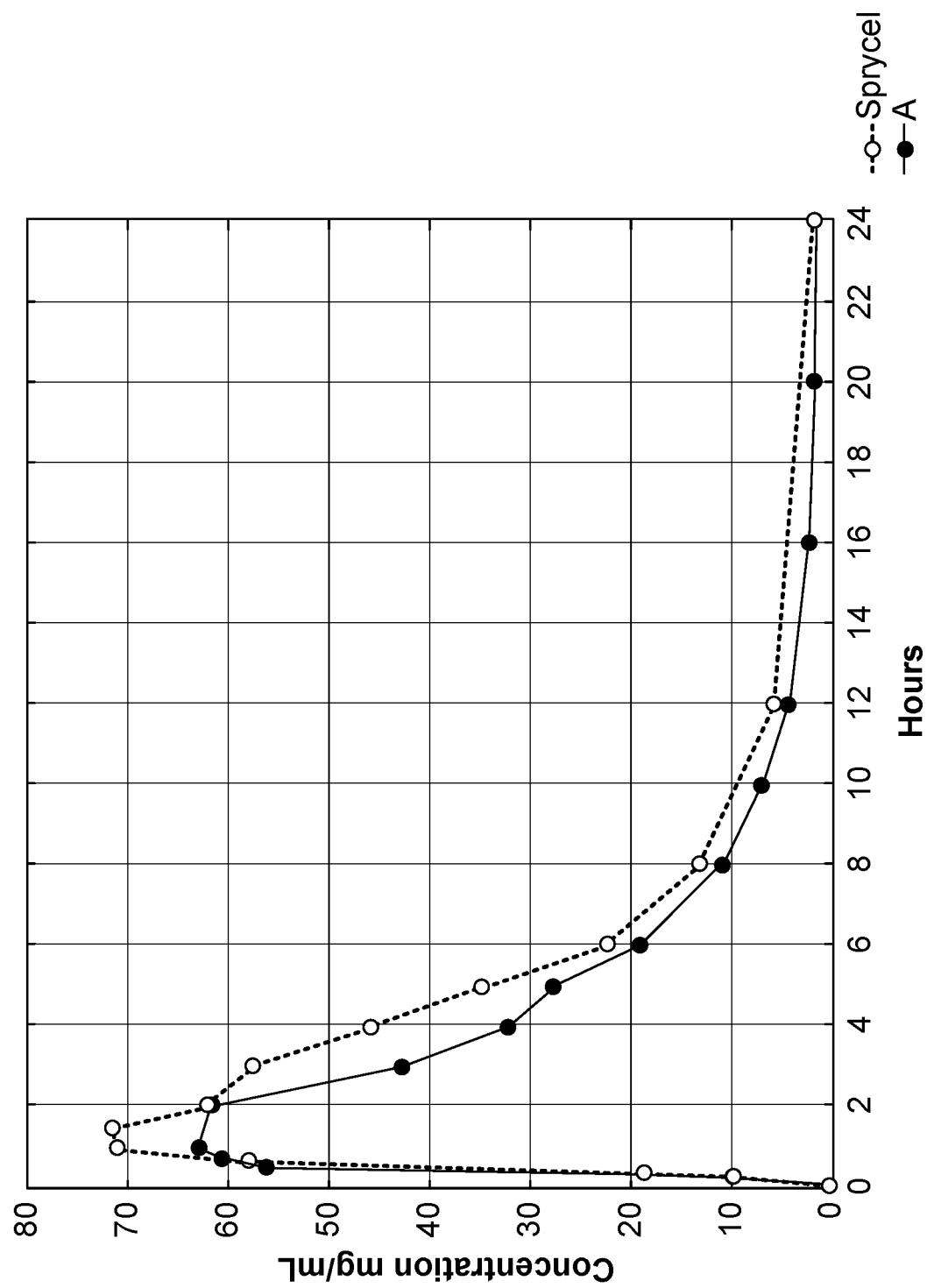
FIG. 2 displays the results showing comparable bioavailability between the test tablet A and the reference product, Sprycel® 100 mg.

The PK variables Cmax, AUC(0-24) and AUC(0-∞) of the test formulation A in the fasted state were compared to the historical PK data of the reference drug, Sprycel, obtained from the previous BA/BE studies. FIG. 2 displays the results showing comparable bioavailability between the test tablet A and the reference product, Sprycel® 100 mg.

| Dependent | FormRef | Test | Ratio_%Ref_ | CI_90_Lower | CI_90_Upper |
|---|---|---|---|---|---|
| Ln (AUCinf) | Sprycel | A fasted | 93 | 73 | 119 |
| Ln (Cmax) | Sprycel | A fasted | 97 | 77 | 121 |

The subject matter of U.S. Provisional Application Nos. 62/849,256 and 62/909,913 is incorporated by reference in its entirety.

The references described herein are incorporated by reference in their entirety to the extent necessary. In the event that there is a difference in meaning between the incorporated terms and the terms disclosed herein and the terms of the related application, the meaning of the terms disclosed herein and the related application will control.

The subject matter of each of U.S. patent application Ser. No. 16/700,310, filed Dec. 2, 2019; U.S. Provisional Application No. 62/849,256, filed on May 17, 2019; and U.S. Provisional Application No. 62/909,913, filed on Oct. 3, 2019 is incorporated by reference in its entirety.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

The invention claimed is:
1. A tablet for oral administration, comprising
dasatinib (S)-1,2-propanediol solvate;
at least one pharmaceutically acceptable excipient; and
a coating layer;
wherein the tablet releases at least 80% of the dasatinib within 20 minutes when the tablet is tested in a USP

Type 2 apparatus in 500 mL of 0.01 M hydrochloric acid at about 37° C. and about 75 RPM;
wherein the amount of dasatinib is equivalent to 50 mg dasatinib.

2. The tablet of claim 1, wherein the at least one pharmaceutical acceptable excipient comprises at least one filler/binder selected from a group consisting of mannitol, microcrystalline cellulose, lactose, isomalt, or a mixture thereof.

3. The tablet of claim 1, wherein the at least one pharmaceutical acceptable excipient comprises at least one filler/binder and the at least one filler/binder is present in an amount of from about 20% to about 90% by weight of the tablet.

4. The tablet of claim 1, wherein the at least one pharmaceutical acceptable excipient comprises at least one filler/binder and the at least one filler/binder is present in an amount of from about 30% to about 80% by weight of the tablet.

5. The tablet of claim 1, wherein the at least one pharmaceutical acceptable excipient comprises at least one disintegrant selected from a group consisting of croscarmellose sodium, crospovidone, sodium starch glycolate, or a mixture thereof.

6. The tablet of claim 1, wherein the at least one pharmaceutical acceptable excipient comprises at least one disintegrant and the disintegrant is present in an amount of from about 0.5% to about 10% by weight of the tablet.

7. The tablet of claim 1, wherein the at least one pharmaceutical acceptable excipient comprises at least one disintegrant and the disintegrant is present in an amount of from about 2% to about 10% by weight of the tablet.

8. The tablet of claim 1, wherein the at least one pharmaceutical acceptable excipient comprises at least one glidant selected from a group consisting of anhydrous colloidal silica.

9. The tablet of claim 1, wherein the at least one pharmaceutical acceptable excipient comprises at least one glidant and the glidant is present in an amount of from about 0% to about 5% by weight of the tablet.

10. The tablet of claim 1, wherein the at least one pharmaceutical acceptable excipient comprises at least one glidant and the glidant is present in an amount of from about 1% to about 4% by weight of the tablet.

11. The tablet of claim 1, wherein the at least one pharmaceutical acceptable excipient comprises at least one lubricant selected from a group consisting of sodium stearyl fumerate, magnesium stearate, or a mixture thereof.

12. The tablet of claim 1, wherein the at least one pharmaceutical acceptable excipient comprises at least one lubricant and the lubricant is present in an amount of from about 0% to about 5% by weight.

13. The tablet of claim 1, wherein the at least one pharmaceutical acceptable excipient comprises at least one lubricant and the lubricant is present in an amount of from about 1% to about 4% by weight.

14. The tablet of claim 1, wherein the coating layer comprises glyceryl monostearate, hypromellose, poly(vinyl alcohol), polyethylene glycol, polysorbate 80, sodium laurylsulfate, talc, titanium dioxide, or a combination thereof.

15. The tablet of claim 1, wherein the coating layer is present in an amount of from about 1.9% to about 2.2% by weight of the tablet.

16. The tablet of claim 1, wherein the tablet exhibits (a) a 90% Confidence Interval for the ratio of the mean AUC (0-∞) which is between 80% and 125%; and (b) a 90% Confidence Interval for the ratio of the mean Cmax, which is between 80% and 125%; and
wherein the ratio of the mean refers to an observable of the tablet for oral administration versus a reference listed drug comprising dasatinib monohydrate.

17. The tablet of claim 1, wherein the tablet exhibits (a) a 90% Confidence Interval for the ratio of the mean AUC (0-∞) which is between 80% and 125%; and (b) a 90% Confidence Interval for the ratio of the mean Cmax, which is between 80% and 125%; and
wherein the ratio of the mean refers to an observable of the tablet for oral administration versus a reference listed drug comprising dasatinib monohydrate;
and wherein the 90% Confidence Interval for the ratio of the mean AUC (0-∞) is established by excluding subjects with AUC (0-∞) less than 5% of the reference listed drug.

18. The tablet of claim 1, wherein the tablet exhibits at least one of the following characteristics: (a) a 90% Confidence Interval for the ratio of the mean AUC (0-00) which is between 80% and 125%; (b) a 90% Confidence Interval for the ratio of the mean Cmax, which is between 80% and 125%; and (c) a RSABE AUC criterion;
and (d) a RSABE Cmax criterion; and
wherein the ratio of the mean refers to an observable of the tablet for oral administration versus a reference listed drug comprising dasatinib monohydrate.

19. The tablet of claim 1, wherein the tablet exhibits at least one of the following characteristics: (a) a 90% Confidence Interval for the ratio of the mean AUC (0-00) which is between 80% and 125%; (b) a 90% Confidence Interval for the ratio of the mean Cmax, which is between 80% and 125%; and (c) a RSABE AUC criterion;
and (d) a RSABE Cmax criterion; and
wherein the ratio of the mean refers to an observable of the tablet for oral administration versus a reference listed drug comprising dasatinib monohydrate;
and wherein the 90% Confidence Interval for the ratio of the mean AUC (0-∞) is established by excluding subjects with AUC (0-∞) less than 5% of the reference listed drug.

20. A method of treating a proliferative disorder in a patient in need thereof, comprising administering a therapeutically effective amount of a composition according to claim 1; wherein said proliferative disorder in a patient is newly diagnosed adults with Philadelphia chromosome-positive (Ph+) chronic myeloid leukemia (CML) in chronic phase; adults with chronic, accelerated, or myeloid or lymphoid blast phase Ph+CML with resistance or intolerance to prior therapy including imatinib; or adults with Philadelphia chromosome-positive acute lymphoblastic leukemia (Ph+ ALL) with resistance or intolerance to prior therapy.

* * * * *